(12) United States Patent
Mady

(10) Patent No.: US 6,328,764 B1
(45) Date of Patent: Dec. 11, 2001

(54) PRIMARY AXIS PROSTHETIC JOINT DESIGN

(76) Inventor: Attila Mady, 126 W. Maryland Ave., Phoenix, AZ (US) 85013-1207

( * ) Notice: Subject to any disclaimer, the term of this patent is extended or adjusted under 35 U.S.C. 154(b) by 4 days.

(21) Appl. No.: 09/509,881

(22) PCT Filed: Apr. 30, 1999

(86) PCT No.: PCT/CA99/00379

§ 371 Date: Jul. 24, 2000

§ 102(e) Date: Jul. 24, 2000

(87) PCT Pub. No.: WO99/58085

PCT Pub. Date: Nov. 18, 1999

Related U.S. Application Data

(60) Provisional application No. 60/084,823, filed on May 8, 1998.

(51) Int. Cl.$^7$ ........................................ A61F 2/34
(52) U.S. Cl. ........................................ 623/22.16
(58) Field of Search .............. 623/22.21, 22.23, 623/22.24, 22.25, 22.28, 22.29, 22.15, 22.16, 22.17, 22.18, 22.19, 22.2

(56) References Cited

U.S. PATENT DOCUMENTS

| | | | |
|---|---|---|---|
| 3,723,995 | * | 4/1973 | Baumann ........................... 623/22.16 |
| 5,092,898 | * | 3/1992 | Bekki et al. ....................... 623/22.16 |
| 5,556,434 | * | 9/1996 | Epstein et al. ..................... 623/22.16 |
| 5,800,556 | * | 9/1998 | Sanders et al. .................... 623/22.15 |
| 5,989,294 | * | 11/1999 | Marlow ............................... 623/22.2 |

* cited by examiner

*Primary Examiner*—David J. Isabella
(74) *Attorney, Agent, or Firm*—Parsons & Goltry; Robert A. Parsons; Michael W. Goltry

(57) ABSTRACT

An artificial joint for implantation into a subject's body is provided which includes an outer race coupled with fixation means to anchor the outer race within an existing joint socket. An inner race member seats within the outer race and a first bearing member is juxtaposed therebetween. The first bearing member has its normal axis closely coincident with a center of rotation that is normal to an axis of most frequent movement of the joint. The bearing component is installed in an alignment that supports loads on a primary axis. A second bearing member may be provided between the inner and outer race members which constrains forces generated during use of the joint and centers forces onto the first bearing member.

7 Claims, 2 Drawing Sheets

PRIMARY AXIS PROSTHETIC JOINT DESIGN

This application claims benefit of Provisional Application No. 60/084,823 filed May 8, 1999.

TECHNICAL FIELD

The present invention relates to artificial joints, and more particularly to replacement joints for humans and other animals.

BACKGROUND OF THE INVENTION

Failure of a skeletal joint in any animal can be a crippling or even fatal occurrence. Joint failure can result from disease, trauma or wear. To compensate for improper functioning of a joint, animals will often change their behavior, including posture and pattern of movement. These adaptations enjoy limited success, and often reduce loads on damaged joints only to distribute them, inappropriately, to other skeletal and muscular components. This deleterious compensation often leads to secondary, traumatic failures at other vulnerable locations.

Significant developments in the field of joint prosthetics for transplantation have been primarily limited to the second half of this century. Despite substantial advances in surgical techniques, prosthetic materials, and therapies, the life expectancy of artificial joints remains limited. In general, life expectancy depends upon the complexity of the joint repair or replacement surgery, the design of the prosthetic joint device, and the age and weight of the patient. Average hip transplants, for example, will last between 8 to 12 years. The life expectancy of artificial knee joints are even more restricted.

In addition to the poor life expectancy of current artificial joints, the surgery which is required to implant joint prosthetics is particularly invasive. For example, hip replacement surgery often requires a hospital stay of up to two weeks, and several months of rehabilitation. Costs can run in excess of $ 40,000. Thus, in view of both the poor life expectancy, high costs and patient morbidity, joint replacement is generally not performed until it becomes unavoidable. Delaying replacement in this manner causes further damage to otherwise healthy tissues, and unnecessary pain to patients.

To date, a wide variety of artificial replacements for ball and socket joints have been developed. For human hip replacement, several closely related designs have become standards in the industry. These prosthetic devices follow the same basic principles in both design and implementation. In the traditional hip replacement procedure, an artificial socket is first embedded in the patient's acetabulum. The acetabulum is the convergence of the ilium, the ischium and the pubis; a naturally occurring cup or socket that accommodates the femoral head, a ¾ sphere covered with thick tenacious articular cartilage. The replacement ball component, if required, is then attached to the femur and inserted into the artificial socket. In some cases it is possible to retain the patient's natural femoral head.

To retain the ball in the socket, a number of different designs have been developed. In the most common method, referred to herein as a "semi constrained" construction, the patient's muscles, tendons and ligaments, are used to retain the ball within the socket. In these designs, a hemispherical socket is used which accommodates the ball and allows the attached femur a wide range of movement. When installing a semi constrained joint, aligning the ball and socket as closely as possible with the patient's natural anatomy is of key importance. This is to ensure that the patient's movements do not dislocate the ball from the joint.

To increase the stability and avoid post-operative dislocations in such semi-constrained constructions, a cylindrical portion is added to the hemispherical socket to make it deeper. The ball is not physically constrained by the socket, but it does have further to travel than if just a hemisphere is used. Ball and socket joints of this type generally provide an arc or range of motion of approximately 1150.

Dislocation frequencies of less than 5% for hip joint implant procedures using a semi-constrained construction have been reported. However, even a low frequency of dislocations is significant, because dislocation can render the patient immobile and can require a second operation. In this event, the critical alignment required for a semi-constrained construction is even more difficult to achieve. Thus, higher dislocation frequencies are encountered in the case of sequential implantations.

An alternative to the semi-constrained construction is a construction wherein the ball is physically constrained within the socket. In this construction, a spherically shaped bearing surrounds the ball and serves as the socket. The bearing encompasses more than one-half of the ball and thus constrains the ball and femoral component from dislocation. The slide bearings in these artificial joints are typically made from plastics, such as high density polyethylene or metal. The more the bearing encompasses the ball, the smaller the range of motion for the femoral component prior to contact with the bearing. For these constructions, it has been found that a dislocating force is created when the neck of the arm attached to the ball impinges on the rim of the bearing. Because of the leverage associated with the length of the femur the dislocating force produced when the femoral component contacts the rim of the bearing can be substantial. A relatively small force applied to a patient's leg can thus produce a dislocating force of over several hundred pounds, due to the substantial leverages involved. Dislocation forces must therefore be avoided in the same way as dislocations are avoided in the semi-constrained construction, i.e., through precise alignment of the artificial joint with the natural anatomy of the patient.

Artificial hips having this type of constrained architecture have been found to suffer dislocation due to leverage in fewer than 0.5% of the implantations performed. This is significantly better than the dislocation frequency reported for semi-constrained implants, but an even lower dislocation frequency is of course desirable.

In addition to the risks of dislocation, another problem with artificial joint replacement is attributed to deterioration of the prosthetic components. For example, plastic bearings wear out over time. Accompanying this wear, friction and stresses resulting from post-operative use of the joint typically produce particulates which accumulate and hasten failure of the joint. This deterioration often results in substantial pain and damage to the surrounding tissue. In general, deterioration of surrounding tissue, particularly bone mass, which accompanies artificial joint wear renders subsequent implantations more difficult and less likely to yield a successful result.

A fundamental design problem with existing artificial joints is that prosthetic engineers have attempted to recreate, using man-made materials, replicas of naturally occurring joints. Unfortunately, man-made materials are not yet the equal of their natural, living counterparts. They do not do the job as well and they break down more quickly due to the lack of self-repair capacity.

It is therefore an object of the present invention to provide an artificial joint which supplies the patient with a sturdy, durable replacement prosthesis by reducing frictional forces and increasing the strength of the joint so that it will last a patient's life time.

Another object of the invention is to provide an artificial joint which resists post-operative dislocations without sacrificing range of motion.

A further object of the invention is to provide an artificial joint which delivers increased shock absorption and transmission, resulting in more comfortable use by the patient.

Yet another object of the present invention is to provide an artificial joint which allows surgeons a greater degree of latitude in geometric positioning of the joint during surgical implantation than can be achieved with presently available joint prostheses.

SUMMARY OF THE INVENTION

The present invention achieves these objects and satisfies other objects and advantages by providing a novel artificial joint design based on a fundamental departure from previous design perspectives.

Rather than attempting to mimic the architecture of a natural joint, the invention disclosed herein provides uniquely engineered prostheses, constructed with man-made materials, which fit into the anatomical constraints of implant subjects but are not patterned to replicate a natural joint.

In particular, the invention provides a prosthetic joint device for implantation into an animal patient for joint replacement treatment which includes an outer race member sized and dimensioned for implantation within a socket portion of the joint. The outer race member defines a cavity for receiving a bearing assembly and is connected with attachment means for affixing the outer race member within the socket portion of said joint. Also included in the joint implant is a bearing assembly comprised of an inner race member nested within the cavity of the outer race member, and at least first a bearing means rotatably interposed between the outer race member and the inner race member. The inner race member in turn defines a prosthetic socket sized and dimensioned to receive a ball portion of the joint. The first bearing means are constructed and positioned to freely rotate around a primary axis of said joint. In preferred embodiments of the invention, the prosthetic joint device further includes second bearing means rotatably interposed between the outer race member and the inner race member, which second bearing means preferably function to center forces generated by loaded movement and provide a low friction means of constraining the first bearing means to optimally rotate around the normal bearing axis.

It is to be understood, of course, that both the foregoing general description and the following detailed description are explanatory only and are not restrictive of the invention. The accompanying drawings, which are incorporated in and constitute part of the specification, illustrate the preferred embodiments of the invention, and together with the description, serve to explain the principles of the invention.

DESCRIPTION OF THE SPECIFIC EMBODIMENTS

Figure 1:
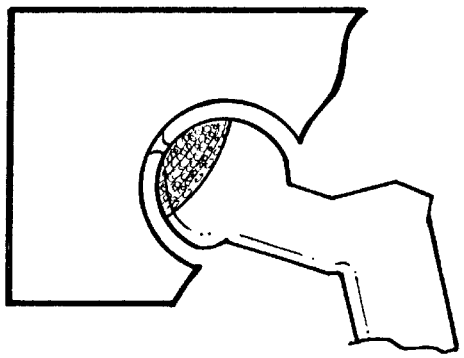
FIG. 1 is a representation of a natural human hip joint.
Figure 2:
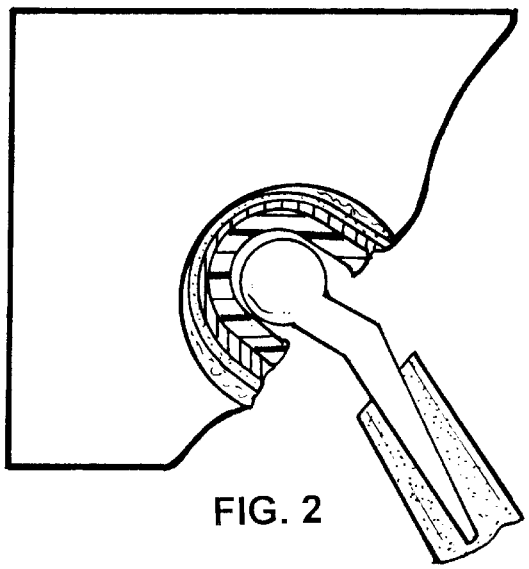
FIG. 2 depicts a conventional joint prosthesis implanted in a human hip.

To facilitate the following description, FIG. 1 depicts the basic anatomy of a natural human hip. The head of the femur is attached to the acetabulum and is constrained within the natural socket by ligaments and muscles surrounding the joint. The interior of the acetabulum is covered in a though but remarkably slick cartilage that is nourished by an artery passing through the center of the joint. In a traditional artificial hip replacement, the cartilage is removed and the natural socket is reamed out to accommodate the man-made socket As shown in FIG. 2, a stainless steel cup is attached within the reamed out acetabulum using cement, screws or other means of attachment. Stainless steel is the most commonly used material for the artificial socket component, although ceramics and other materials have also been used. Within the socket, a slide bearing is placed that is intended to restrain the femoral component within the socket, and to mimic the lubricating function of the original cartilage. The slide bearing is most commonly made of high density polyethylene and supports movement through varying ranges of motion.

Figure 3:
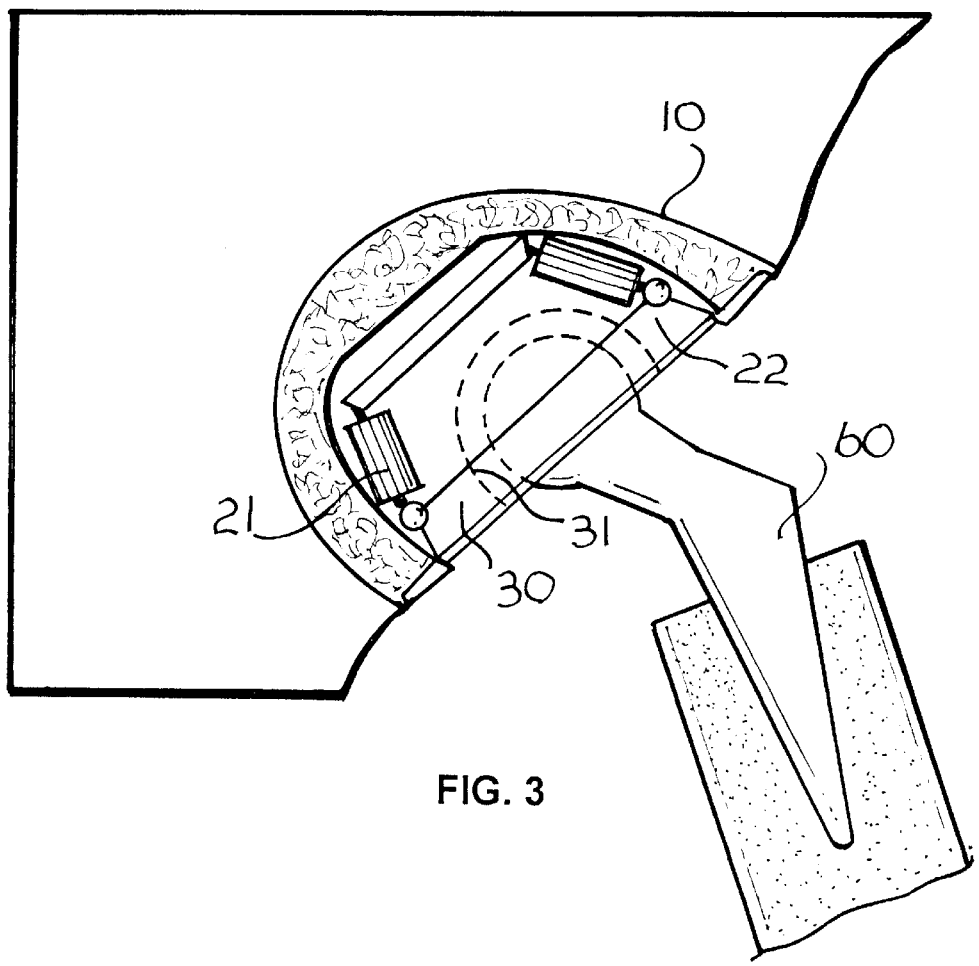
FIG. 3 is a representation of a joint prosthesis exemplifying the concepts of the present invention implanted into a human hip.

As noted above, the present invention departs from previous artificial joint designs in a fundamental manner. Rather than mimicking the natural human hip, the invention provides additional mechanical elements which resolve numerous problems and limitations of previous joint prostheses. To illustrate the basic concepts of the invention, FIG. 3 provides a schematic representation of an exemplary joint prosthesis implanted within a human hip. As in the case of previous artificial joint designs, a socket component is affixed within a socket portion of the joint (e.g., a reamed out socket portion of the acetabulum) in a semi-constrained construction.

In the present invention however, the cup or socket component includes an outer race member 10 sized and dimensioned for implantation within a socket member (e.g., a worn or artificially evaginated socket of an acetabulum or shoulder joint). To fix the outer race member within the natural joint'socket, fixation means are provided to anchor the outer race member within the patient's joint socket. The fixation means preferably comprise conventional set pins which pass through set pin channels 50 in the outer race member and anchor it to the socket. Alternatively, cements and other fixation means are contemplated to achieve this goal.

The outer race member 10 defines a cavity 11 for receiving a bearing assembly 12. The bearing assembly is preferably comprised of an inner race member 30 nested within the cavity, and first bearing means 21 rotatably interposed between the outer race member and inner race member.

The inner race member 30 defines a prosthetic socket 31 sized and dimensioned to receive a ball portion, e.g., a natural or artificial femoral end 60, or humeral end, of the joint. Importantly, the first bearing means 21 are constructed and positioned to freely rotate around a primary axis corresponding to the major load bearing axis of the joint In the case of the human hip, approximately 99-. of loaded movement is along the anterior/posterior axis of joint movement, which axis thereby defines the primary axis. This is also the case for the human shoulder joint. Proper placement and construction of the first bearing means 21 for rotation around the primary axis of the hip joint is illustrated in the drawings (see FIGS. 4 and 5). However, placement and construction of first bearing means in other prosthetic joints within the invention will vary, as will be readily understood and routinely designed by the artisan in accordance with the teachings herein to achieve free movement around the major load bearing axis. In general, the first bearing means 21 are selected and positioned relative to the outer race member 10 and inner race member 30 so that the normal (or defining) axis of the bearing coincides as closely as possible with the center of rotation that subtends, or is normal to, the axis of most frequent movement of the joint.

Figure 4:
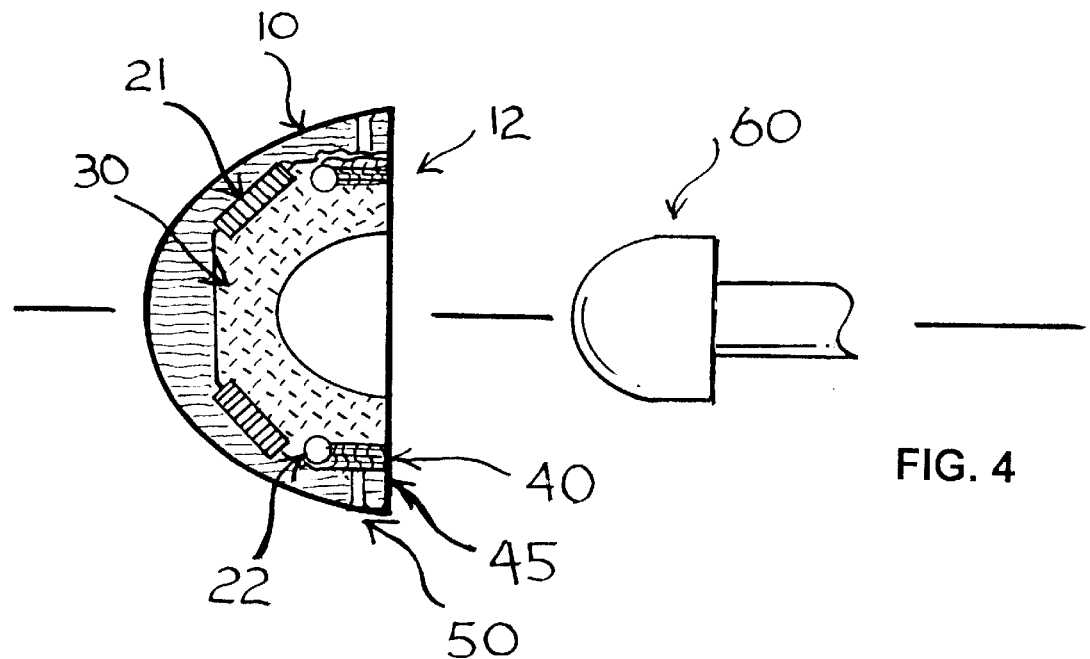
FIG. 4 is a cross sectional view of an assembled bearing assembly of a joint prosthesis exemplifying the concepts of the invention.

The assembled joint in FIG. 4 illustrates an additional component of the invention, which is a retaining mechanism 40 for holding the inner race 30 snugly nested within the outer race 10. As in the case of the attachment means 50, a variety of retaining devices and designs can be employed to achieve this purpose. In preferred aspects of the invention, the retaining mechanism is in the form of a retainer ring which seats via a detent fit or screws into the outer race, e.g., by means of mating threads 45 located along the inner circumference of the outer race and the outer periphery of the retainer ring (FIG. 4).

In preferred embodiments of the invention, the prosthetic joint device also incorporates a dampening mechanism, preferably a second bearing means 22 rotatably interposed between the inner race member 30 and the outer race member 10 or retaining ring 40. In the embodiment shown in FIGS. 4 and 5, the dampening mechanism is comprised of second bearing means which are constructed and positioned to center the forces generated by loaded movement, and to provide a low friction mechanism for constraining the first bearing means 21 to optimally rotate around its normal bearing axis. In this embodiment, the retaining mechanism 40 constrains the second bearing means 22 (eg., ball bearings) within a bearing housing created by wedding of the retainer and inner race 30. This allows the bearings to freely rotate and act as a centering means for the forces generated during use of the joint.

Figure 5:
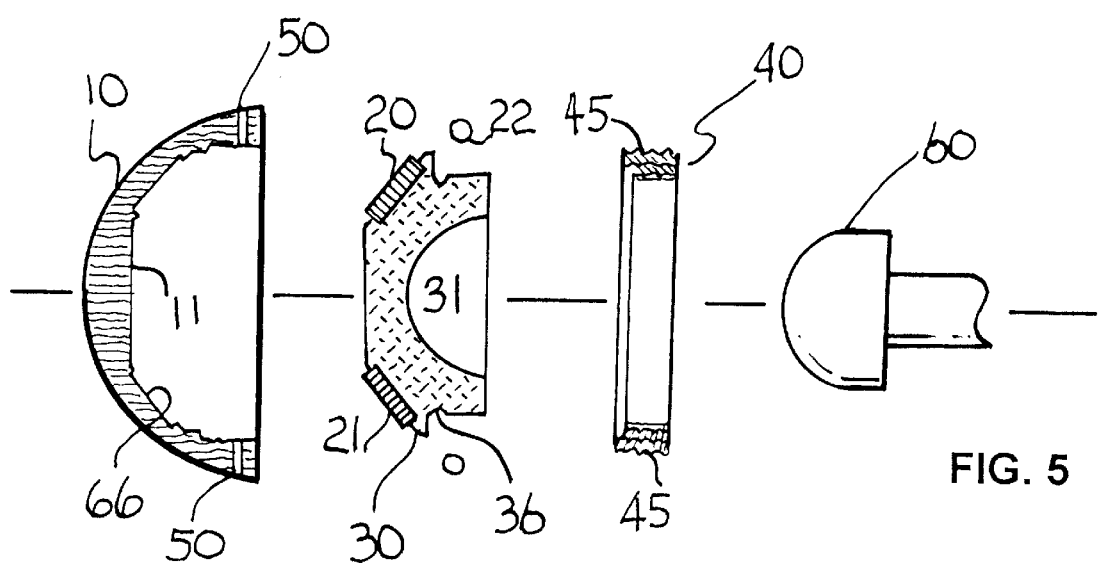
FIG. 5 is an exploded, cross sectional view of a joint prosthesis exemplifying the concepts of the invention.

In more detailed aspects of the invention depicted in FIG. 5 the outer race 10 provides a cavity 11 which is specifically adapted to feature a channel 66 for receiving the bearing cage 20. The cavity also is shaped to closely conform to other components of the bearing assembly 12, including the first bearing means 21 (e.g., roller bearing) and the inner race 30, as well as to receive the retaining means 40. The bearing cage 20 is in the form of a conventional roller bearing cage and is responsible for properly separating and retaining the individual bearing rollers.

In addition to the above described prosthetic joint devices, the invention also provides methods for replacing defective joints in an animal patient. The methods follow conventional surgical joint replacement procedures, wherein the above described artificial joint device is implanted in a defective joint of the patient.

In preferred embodiments of the invention, the above described bearing assembly features a roller bearing as the first bearing means 21 housed in a conventional bearing cage 20, as shown in FIGS. 4 and 5. Also in preferred embodiments, standard ball bearings are provided as the second bearing means 22, seated in a circumferential groove 36 in the inner race 30. In more preferred aspects of the invention, the roller bearing of the bearing assembly 12 is a tapered, roller, thrust bearing and supports loads on the primary axis. The roller bearing is preferably made of surgical-grade stainless steel, or a similarly hard and durable substance.

The use of a steel anti-friction bearing for loaded, movement coincident with the primary axis will allow greatly reduced friction, particulate-free operation, negligible wear and thus, potentially lifetime durability. Roller bearings of this kind are rated for hundreds of millions of revolutions at high frequencies and with peak loads far exceeding those that will be experienced in normal use by a human or other animal subject.

Although the foregoing invention has been described in some detail by way of illustration and example for purposes of clarity of understanding, it will be understood that certain changes and modifications may be practiced within the scope of the appended claims. Thus, in accordance with the foregoing disclosure, the invention is not to be limited by the exemplary, description and drawings herein, but is to be determined in scope by the claims which follow.

What is claimed is:

1. A prosthetic joint device for implantation into a patient for joint replacement treatment, comprising:

an outer race member sized and dimensioned for implantation within a socket portion of said joint and defining a cavity for receiving a bearing assembly; attachment means for affixing said outer race member within said socket portion of said joint; a bearing assembly comprised of an inner race member having an inner surface and an outer surface, nested within said cavity and first bearing means rotatably interposed between said outer race member and said outer surface of said inner race member, said inner surface of said inner race member defining a prosthetic socket sized and dimensioned to receive a ball portion of said joint, wherein said first bearing means are constructed and positioned to permit rotation of the inner race around a primary axis of said joint.

2. The prosthetic joint device of claim 1, further comprising a second bearing means rotatably interposed between said outer race member and said inner race member.

3. The prosthetic joint device of claim 2, wherein the second bearing means are constructed and positioned to center forces generated by loaded movement and provide a low friction means of constraining said first bearing means to optimally rotate around the normal bearing axis.

4. A method for replacing a joint in a patient comprising the step of:

implanting into a defective joint of said patient a prosthetic joint device comprising an outer race member sized and dimensioned for implantation within a socket portion of said joint and defining a cavity for receiving a bearing assembly, attachment means for affixing said outer race member within said socket portion of said joint, a bearing assembly comprised of an inner race member having an inner surface and an outer surface, nested within said cavity and first bearing means rotatably interposed between said outer race member and said outer surface of said inner race member, said inner surface of said inner race member defining a prosthetic socket sized and dimensioned to receive a ball portion of said joint, wherein said first bearing means are constructed and positioned to permit rotation of the inner race around a primary axis corresponding to the major load bearing axis of said joint.

5. The method for replacing the joint of claim 4, wherein the prosthetic joint device further comprises a second bearing means rotatably interposed between said outer race member and said inner race member.

6. The method for replacing the joint of claim 5, wherein the second bearing means are constructed and positioned to center forces generated by loaded movement and provide a low friction means of constraining said first bearing means to optimally rotate around the normal bearing axis.

7. A prosthetic joint device for implantation into a patient for joint replacement treatment, comprising:

a socket assembly including an outer race member sized and dimensioned for implantation within a socket portion of said joint and defining a cavity for receiving a bearing assembly; attachment means for affixing said outer race member within said socket portion of said joint; a bearing assembly comprised of an inner race member having an inner surface and an outer surface, nested within said cavity and first bearing means rotatably interposed between said outer race member and said outer surface of said inner race member, said inner surface of said inner race member defining a prosthetic socket; and a ball portion received within the prosthetic socket, wherein said first bearing means are constructed and positioned to permit rotation of the inner race around a primary axis of said joint, and the ball portion rotates within the prosthetic socket.

\* \* \* \* \*